(12) United States Patent
Van Der Mooren et al.

(10) Patent No.: US 10,379,379 B2
(45) Date of Patent: Aug. 13, 2019

(54) LENS PROVIDING EXTENDED DEPTH OF FOCUS AND METHOD RELATING TO SAME

(71) Applicant: AMO Groningen B.V., Groningen (NL)

(72) Inventors: Marrie H. Van Der Mooren, Engelbert (NL); Hendrik A. Weeber, Groningen (NL); Patricia Ann Piers, Groningen (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 14/196,154

(22) Filed: Mar. 4, 2014

(65) Prior Publication Data

US 2014/0257480 A1 Sep. 11, 2014

Related U.S. Application Data

(60) Provisional application No. 61/774,009, filed on Mar. 7, 2013, provisional application No. 61/817,693, filed on Apr. 30, 2013.

(51) Int. Cl.
| | |
|---|---|
| *A61F 2/14* | (2006.01) |
| *A61F 2/16* | (2006.01) |
| *G02C 7/02* | (2006.01) |
| *G02B 27/00* | (2006.01) |
| *G02C 7/04* | (2006.01) |

(52) U.S. Cl.
CPC .............. *G02C 7/028* (2013.01); *A61F 2/164* (2015.04); *A61F 2/1618* (2013.01); *G02C 7/042* (2013.01); *A61F 2/14* (2013.01); *A61F 2/1613* (2013.01); *G02B 27/0075* (2013.01)

(58) Field of Classification Search
None
See application file for complete search history.

(56) References Cited

U.S. PATENT DOCUMENTS

| | | | |
|---|---|---|---|
| 3,583,790 A * | 6/1971 | Baker ........................... | 359/676 |
| 5,748,371 A | 5/1998 | Cathey, Jr. et al. | |
| 6,069,738 A | 5/2000 | Cathey, Jr. et al. | |
| 6,536,898 B1 * | 3/2003 | Cathey, Jr. ............... | 351/159.03 |
| 7,209,293 B2 * | 4/2007 | Gaida et al. .................. | 359/656 |
| 2003/0225455 A1 | 12/2003 | Cathey et al. | |
| 2004/0156013 A1 * | 8/2004 | Lindacher ............. | A61F 2/1613 |
| | | | 351/159.41 |
| 2005/0204329 A1 * | 9/2005 | Pauca ..................... | G06T 5/003 |
| | | | 716/55 |

(Continued)

FOREIGN PATENT DOCUMENTS

EP 2302421 A1 3/2011

OTHER PUBLICATIONS

International Search Report and Written Opinion for Application No. PCT/IB2014/000914, dated Oct. 17, 2014, 11 pages.

*Primary Examiner* — Leslie Lopez
(74) *Attorney, Agent, or Firm* — Johnson & Johnson Surgical Vision, Inc.

(57) ABSTRACT

Ophthalmic lenses providing an extended depth of focus include anterior and posterior faces, wherein at least part of the anterior or posterior face has a curvature based upon the summation of a cubic and/or pentic phase profile, and methods relating to same. The ophthalmic lens may be a contact lens, an intraocular lens (IOL), or other corrective lens.

4 Claims, 16 Drawing Sheets

(56) References Cited

U.S. PATENT DOCUMENTS

2006/0274262 A1   12/2006  Andino et al.
2010/0094413 A1*  4/2010  Rombach et al. ........... 623/6.25
2010/0097569 A1   4/2010  Weeber et al.
2012/0143326 A1   6/2012  Canovas Vidal et al.

* cited by examiner

LENS PROVIDING EXTENDED DEPTH OF FOCUS AND METHOD RELATING TO SAME

CROSS-REFERENCES TO RELATED APPLICATIONS

This application claims priority to U.S. provisional application No. 61/817,693 filed on Apr. 30, 2013 and U.S. provisional application No. 61/774,009 filed on Marcy 7, 2013, the entire contents of both of which are incorporated herein by reference.

BACKGROUND OF THE INVENTION

Field of the Invention

The field of the present invention is lenses providing extended depth of focus, particularly ophthalmic lenses such as contact lenses, corneal inlays or onlays, and/or intraocular lenses (IOLs).

Description of the Background

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia, which normally develops as a person ages but which may additionally develop due to certain conditions of the eye, is associated with a sudden or progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only a limited ability to change shape.

Along with reductions in accommodation of the eye, age may also induce clouding of the lens due to the formation of a cataract. A cataract may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL".

Monofocal IOLs are intended to provide vision correction at one distance only, usually the far focus. Predicting the most appropriate IOL power for implantation has limited accuracy, and an inappropriate IOL power can leave patients with residual refraction errors following surgery. Accordingly, it may be necessary for a patient who has received an IOL implant to also wear spectacles to achieve good far vision. At the very least, since a monofocal IOL provides vision treatment at only one distance and since the typical correction provided by the monofocal IOL is for far distance, spectacles are usually needed for good near and sometimes intermediate vision following implantation of a typical monofocal IOL.

The term "near vision" generally corresponds to vision provided when objects are at a distance from the subject eye of between about 1 to 2 feet are substantially in focus on the retina of the eye. The term "distant vision" generally corresponds to vision provided when objects at a distance of at least about 6 feet or greater are substantially in focus on the retina of the eye. The term "intermediate vision" generally corresponds to vision provided when objects at a distance of about 2 feet to about 6 feet from the subject eye are substantially in focus on the retina of the eye.

There have been various attempts to address the foregoing and other limitations associated with monofocal IOLs. For example, multifocal IOLs have been proposed that deliver, in principle, two foci, one near and one far, optionally with some degree of intermediate focus. Such multifocal, or bifocal, IOLs are intended to provide good vision at two distances, and include both refractive and diffractive multifocal IOLs. In some instances, a multifocal IOL intended to correct vision at two distances may provide a near add power of about 3.0 or 4.0 diopters, by way of non-limiting example.

Like monofocal lenses, multifocal lenses may take the form of an intraocular lens placed within the capsular bag of the eye, replacing the original lens or placed in front of the natural crystalline lens. Corrective monofocal or multifocal ophthalmic lenses may also be in the form of a contact lens or in the form of any other type of corrective lens placed not within the capsular bag of the eye, but rather placed external to but within the visual field of the eye.

Although multifocal ophthalmic lenses often lead to improved quality of vision for many patients, additional improvements would be beneficial. For example, some pseudophakic patients experience undesirable visual effects (dysphotopsia), e.g. glare or halos. Halos may arise when light from the unused focal image creates an out-of-focus image that is superimposed on the used focal image. For example, if light from a distant point source is imaged onto the retina by the distant focus of a bifocal IOL, the near focus of the IOL will simultaneously superimpose a defocused image on top of the image formed by the distant focus. This defocused image may manifest itself in the form of a ring of light surrounding the in-focus image, and is referred to as a halo. Another area in need of improvement revolves around the typical bifocality of multifocal lenses. More particularly, since multifocal ophthalmic lenses typically provide for near and far vision, intermediate vision may be compromised.

A lens with an extended depth of focus (EDOF, also referred to herein as extended depth of field) may remedy these disadvantages of known corrective lenses, at least in that an EDOF lens may provide certain patients the benefits of good vision at a range of distances, while having reduced or no dysphotopsia. Various techniques for extending the depth of focus of an IOL have been previously proposed. For example, some approaches are based on a bulls-eye refractive principle, and involve a central zone with a slightly increased power. Other techniques include an asphere or include refractive zones with different refractive zonal powers.

Although certain such lenses or lens combinations and/or treatments may provide some benefit to some patients, further advances, particularly with respect to EDOF lenses are desirable to benefit even more patients. For example, a further improved IOL lens which confers enhanced image quality across a wide and extended range of foci without dysphotopsia is desirable.

SUMMARY OF THE INVENTION

The present invention is generally directed toward a lens providing an extended depth of focus through incorporation of one or more higher order curvature profiles into portions of an anterior or posterior face of the lens, and methods relating to same. Such lenses may provide improved ophthalmic lenses, such as contact lenses, corneal inlays or onlays, or intraocular lenses (IOLs) including, for example, phakic IOLs and piggyback IOLs.

In an aspect of the present invention, the anterior and/or posterior face of the lens has curvature based upon a cubic phase profile and/or pentic phase profile. In another aspect, the anterior and/or posterior face of the lens has a curvature based upon the summation of an aspheric profile and the one or more higher order curvature profiles, which include a cubic phase profile and/or pentic phase profile. The overall optical profile of such a lens is designed such that it increases the depth of focus of the pseudophakic eye, in which eye the natural crystalline lens of the eye is substituted with a synthetic lens. Such a singular IOL technique suppresses the distinct bifocality associated with traditional multifocal IOLs which have many diffractive rings.

In embodiments of the present invention, one of the anterior or posterior face includes a first profile comprised of the one or more higher order curvature profiles, which include a cubic and/or pentic phase profile. The first profile may be a refractive profile, a diffractive profile, or any combination thereof, and portions of the first profile may have curvatures that are defined by parabolic, hyperbolic, spherical, aspheric, and/or sinusoidal curves, or any combination thereof, prior to incorporation of the one or more higher order profiles. The first profile may also include transition portions into which the one or more higher order profiles may be incorporated.

Accordingly, an improved lens having an extended depth of focus, and a method relating to same, is disclosed. Advantages of the present invention will appear from the drawings and the detailed description of the embodiments.

BRIEF DESCRIPTION OF THE DRAWINGS

Reference is made to the accompanying drawings, in conjunction with the ensuing detailed description, for a fuller understanding of the nature and advantages of the invention. In the drawings, like reference numerals refer to similar components, and.

DETAILED DESCRIPTION

Figure 1:
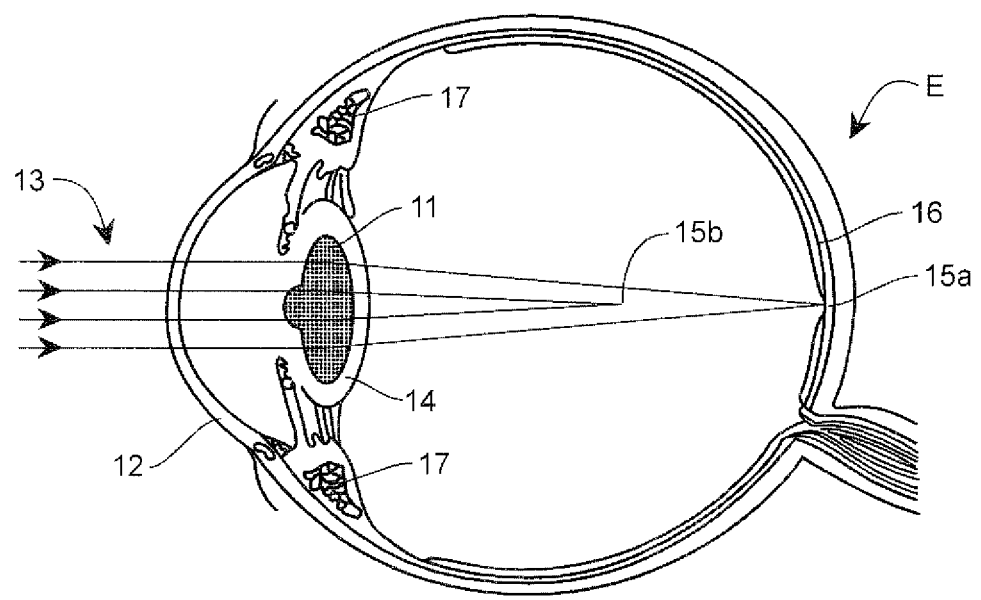
FIG. 1 is a cross-sectional view of an eye having an implanted refractive intraocular lens.

The figures and descriptions of the present invention have been simplified to illustrate elements that are relevant for a clear understanding of the present invention, while eliminating, for the purpose of clarity and brevity, many other elements found in typical ophthalmic lenses and implantable optic apparatuses, systems and methods. Those of ordinary skill in the art may thus recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Embodiments of the present invention encompass lenses and lens systems that provide improved image quality over an extended range of focal points or foci. Such lenses and lens systems may encompass various ophthalmic lenses such as, for example, contact lenses, intraocular lenses, spectacle lenses, and corneal inlays or onlays. Exemplary embodiments include ophthalmic lenses having an extended depth of focus, as compared to conventional monofocal lenses, and providing reduced dysphotopsia as compared to conventional multifocal ophthalmic lenses. Advantageously, such ophthalmic lenses can provide a patient with improved distance vision, as well as improved vision at intermediate distances without dysphotopsia.

Embodiments of the present invention generally provide improved lenses and imaging systems and may be incorporated into any system in which a lens with an extended depth of focus may be advantageous, such as camera lenses (still and video), including those used for surveillance or for surgical procedures, as well as for cameras in mobile phones or other related devices. Embodiments of the invention may find their most immediate use in the form of improved ophthalmic devices, systems, and methods.

Exemplary embodiments of the present invention may provide improved ophthalmic lenses (including, for example contact lenses, intraocular lenses (IOLs), corneal implants and the like) and associated methods for their design and use. Embodiments of the present invention may be used with monofocal diffractive or refractive lenses, bifocal diffractive or refractive lenses, and multifocal diffractive or refractive lenses, e.g. embodiments of the present invention could be added to the opposite surface of multifocal IOLs, In other words, an extended depth of focus feature may be added to, for example, the opposite surface of a diffractive or refractive multifocal embodiment. In addition, an extended depth of focus feature may be added to, for example, a toric IOL, an IOL that modifies ocular spherical and/or chromatic aberration, and/or an accommodating IOL. In general, an extended depth of focus feature may be added to an IOL that modifies ocular aberrations.

In a non-limiting situation to which the present invention is particularly applicable, reading is often done in bright light conditions in which the pupil is small. In contrast, night-time driving is done in low light conditions in which the pupil is large. Embodiments of the present invention encompass lenses that relatively emphasize intermediate or near vision for small pupil sizes, while also relatively emphasizing far vision for large pupil sizes. In some such ophthalmic lenses, a greater proportion of light energy may be transmitted to the far focus from a peripheral portion of the lens to accommodate for low light, i.e., for far viewing conditions such as night time driving. Further, in certain situations the near or intermediate focus may receive relatively more light energy than a central portion of the diffractive profile—for reading or computer work, for example, and/or to provide depth of focus and intermediate or near viewing under low light reading conditions, such as, for example, when reading restaurant menus.

FIG. 1A is a cross-sectional view of an eye E fit with a refractive IOL 11 having an aspheric profile. As shown, the refractive IOL 11 may comprise a monofocal IOL, a bifocal IOL, a multifocal IOL. The refractive IOL 11 receives light from at least a portion of the cornea 12 at the front of the eye E and is generally centered about the optical axis of the eye E. For ease of reference, FIG. 1A does not disclose the refractive properties of other parts of the eye, such as the corneal surfaces. Only the refractive properties of the refractive IOL 11 are illustrated.

Each major face of the IOL 11, including the anterior (front) face and posterior (back) face, generally has a refractive profile, e.g. biconvex, plano-convex, plano-concave, meniscus, and the like. The two faces together, in relation to the properties of the surrounding aqueous humor, cornea, and other optical components of the overall optical system, define the effects of the IOL 11 on the imaging performance of the eye E. Conventional, monofocal IOLs have a refractive power based on the refractive index of the material from which the lens is made and on the curvature or shape of the front and rear faces of the IOL.

In a young healthy eye, contraction and relaxation of ciliary muscles 17 surrounding the capsular bag 14 contribute to accommodation of the eye, the process by which the eye increases optical power to maintain focus on objects as they move closer. By way of example, as a person ages, the degree of accommodation decreases and presbyopia, the diminished ability to focus on near objects, often results. A patient may therefore conventionally use a multifocal IOL incorporating two discrete corrective optics, each having a different optical power, one for near vision and one for far vision.

Multifocal refractive lenses may optionally include more than two discrete corrective optics in different regions of the lens, each with a different power so as to mitigate the effects of presbyopia, and/or to provide an extended depth of focus. For example, a perimeter region of a refractive multifocal lens may have a power which is suitable for viewing at far viewing distances. The same refractive multifocal lens may also include an inner region having a higher surface curvature and a generally higher overall power (sometimes referred to as a positive add power) suitable for viewing at near distances.

Multifocal diffractive lenses utilize a similar concept, in that different regions of the lens incorporate discrete corrective optics, with each region having a different power, except that multifocal diffractive lenses generally rely on diffraction to provide an extended depth of focus. U.S. patent application Ser. No. 12/971,506, filed Dec. 17, 2010, the disclosure of which is incorporated herein by reference in its entirety, discloses a multifocal diffractive lens having one or more isolated regions or "echelettes," with each echelette providing a different optical power through diffractive optics.

The depth of focus of the entirety of any one of the foregoing lenses, or of any portion thereof, whether refractive or diffractive, may be enhanced by incorporation of a cubic phase profile into the lens or lens portion. The incorporating lens or lens portion may be on the anterior or posterior face of the lens. The cubic phase profile may be incorporated into the lens or lens portion by mathematical summation of a base profile for the lens or lens portion and the cubic phase profile. The base profile may have a curvature that is defined by parabolic, hyperbolic, spherical, aspheric, and/or sinusoidal curves, or by any combination thereof, so that the overall profile is given by the equation:

Profile=Base Profile+Cubic Phase Profile.

The base profile is preferably optimized for desired focal properties prior to incorporation of the cubic phase profile. More preferably, the base profile may have an aspheric component, with at least the aspheric component being optimized prior to incorporation of the cubic phase profile.

The cubic phase profile has a curvature that is defined by the following function:

$$f(x,y)=A(x^3+y^3),$$

wherein A is a scalar value that may be optimized to achieve the desired depth of field.

Hereinbelow is discussed the incorporation of a cubic phase profile, along with optional higher order phase profiles, into a full lens profile. However, although the following description is within the context of a full lens profile, those of skill in the art will recognize that the additional profiles may be incorporated into any lens profile portion to extend the depth of field of that lens portion.

The use of a cubic phase plate may extend the depth of field by encoding object wavefront information, thus allowing the wavefront to pass through the optical system without being lost to defocus. A cubic phase plate defined by the cubic phase profile described herein may be combined with a monofocal diffractive, or other refractive and diffractive multifocal lenses, for example; and/or with other accommodating lens platforms, tonic lenses, and the like, for example. In addition, a cubic phase plate defined by the discussed cubic phase profile may be applied to only a portion of the IOL surface. For example, a cubic phase plate may only cover a central zone of the IOL surface. By way of further non-limiting example, the cubic phase plate may be applied on a specific zone of a zonal multifocal IOL.

Figure 2A:
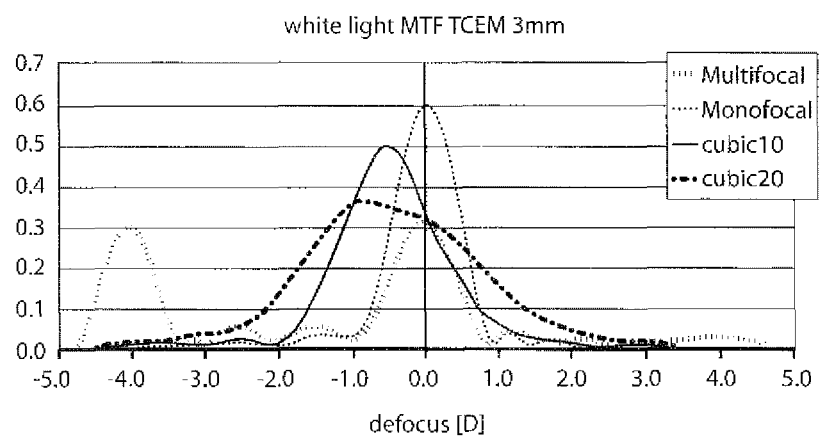
FIGS. 2A and 2B illustrate modeled modulation transfer function (MTF)-defocus curve comparisons for white light between lenses according to embodiments of the invention.
Figure 2B:
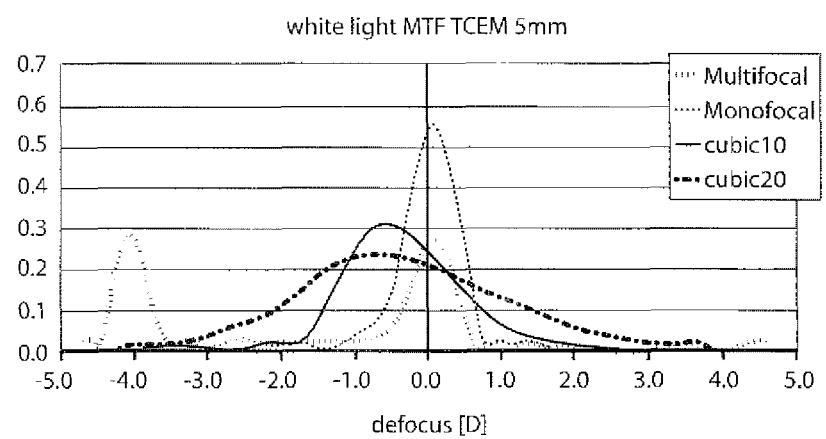

FIGS. 2A and 2B compare the defocus of a monofocal aspheric IOL and a multifocal aspheric IOL with two different IOLs incorporating a cubic phase profile. These defocus profiles are based on simulations for 20 D lenses and are generated for white light modulation transfer functions (MTFs). For the cubic phase profile IOLs, the defocus profiles are taken along the meridian of each simulated IOL. The model that is used for the simulations is based upon a rotationally symmetric theoretical eye model. This same model is used for all simulated data presented herein. In FIG. 2A, the white light MTF is about 50 c/mm and is presented for a simulated 3 mm pupil, and in FIG. 2B the white light MTF is about 50 c/mm and is presented for a simulated 5 mm pupil. In each of FIGS. 2A and 2B, the model labeled "cubic10" assigns a value of −0.0010 to the scalar in the cubic phase profile, and the model labeled "cubic20" assigns a value of −0.0020 to the scalar in the cubic phase profile. This same naming convention is used throughout this description for all simulated data. In each of FIGS. 2A and 2B, the defocus profiles are presented across 4 D in an IOL plane. One of ordinary skill in the art would recognize that 4 D in the IOL plane is approximately the equivalent of 3 D in the spectacle plane.

As can be seen from the simulations presented in both FIGS. 2A and 2B, the depth of focus for each of the cubic10 and cubic 20 profiles is extended as compared to the monofocal and multifocal lenses. In practice, it is anticipated that the natural aspheric aberrations present in the cornea would further extend the depth of focus as compared to the simulated data, which uses a rotationally symmetric eye model. In addition, because of the extended depth of focus, a lens incorporating a cubic phase profile is anticipated to improve halo and glare performance with respect to a multifocal lens.

Figure 3A:
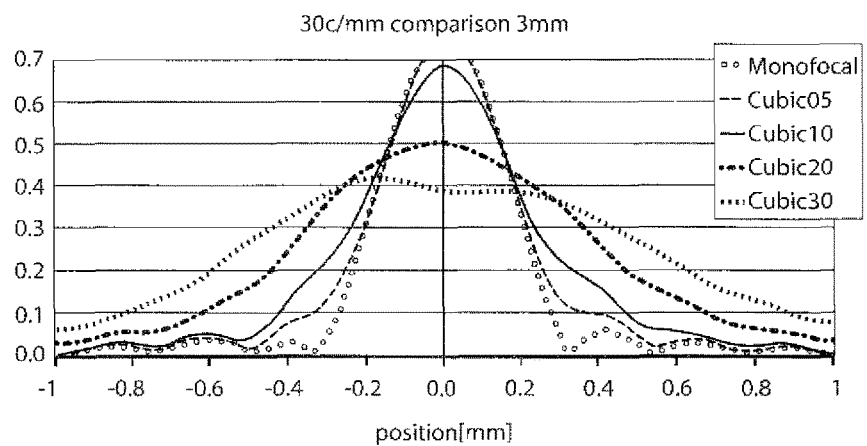
FIGS. 3A-3C illustrate modeled MIT-defocus curve comparisons for white light and a 3 mm pupil between lenses according to embodiments of the invention.
Figure 3B:
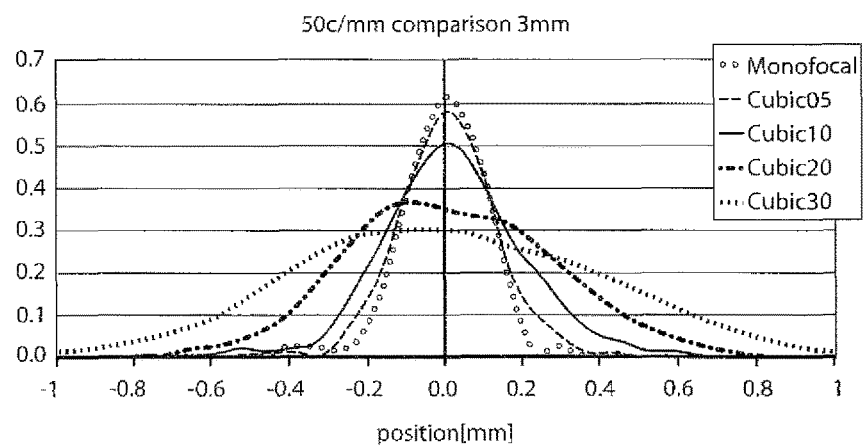
Figure 3C:
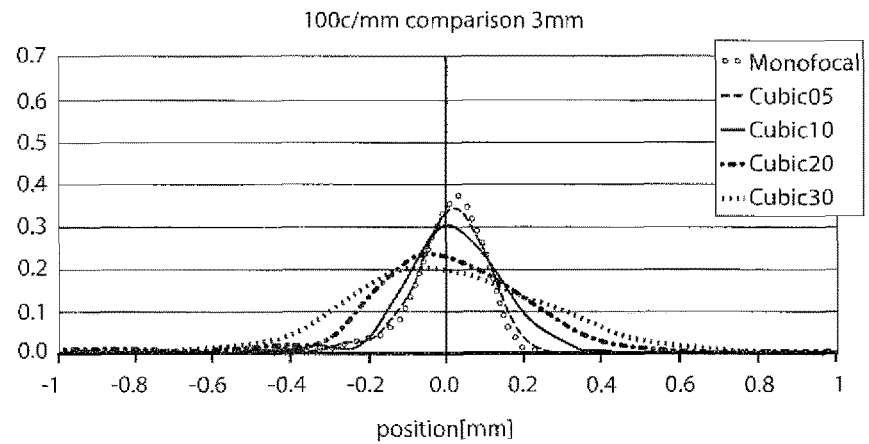

FIGS. 3A-3C show simulated white light MTF results, at three different spatial frequencies for simulated IOLs incorporating a cubic phase profile, using a 3 mm pupil and the same rotationally symmetric theoretical eye model discussed above, and includes a comparison of those profiles to a monofocal IOL. In each of these comparisons, the defocus profiles are presented in millimeters, with 1 mm being approximately 4 D in the IOL plane. As can be seen from the simulations presented in FIGS. 3A-3C, the depth of focus for each of the lens profiles incorporating a cubic phase profile is extended as compared to the monofocal lens.

Figure 4A:
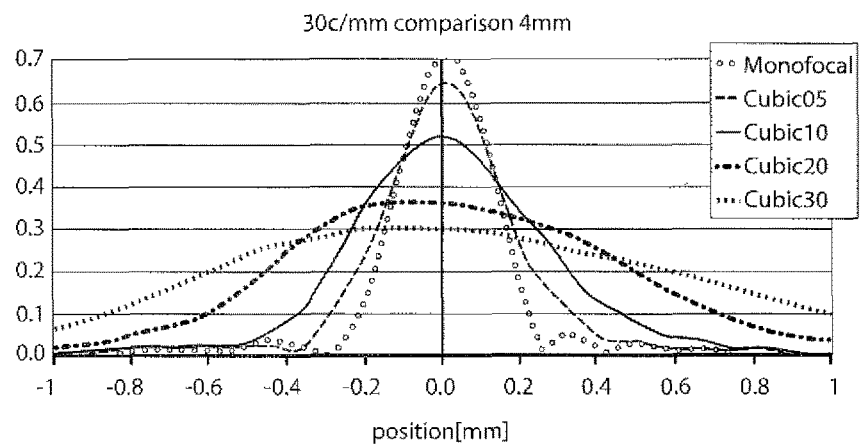
FIGS. 4A-4C illustrate modeled MTF-defocus curve comparisons for white light and a 4 mm pupil between lenses according to embodiments of the invention.
Figure 4B:
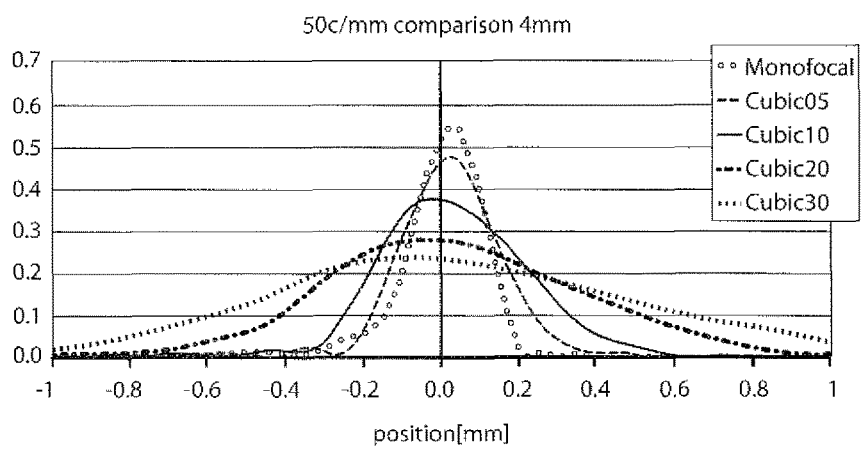
Figure 4C:
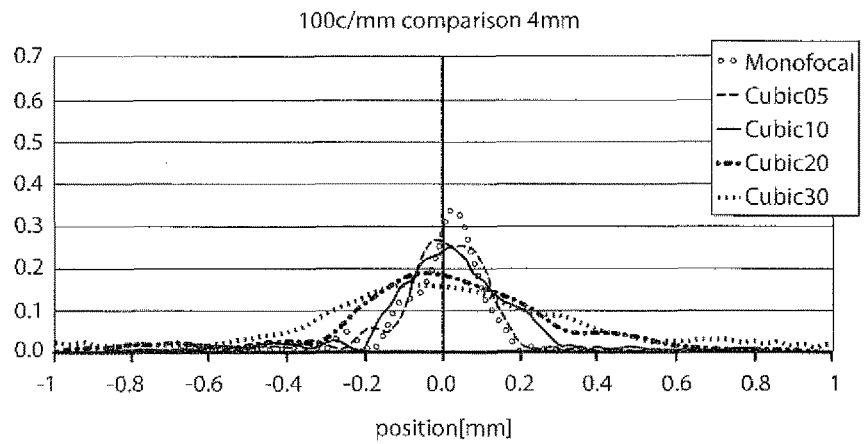

FIGS. 4A-4C show simulated white light MTF results at three different spatial frequencies for simulated IOLs incorporating a cubic phase profile using a 4 mm pupil and the same rotationally symmetric theoretical eye model, and comparing those profiles to a monofocal IOL. In each of these comparisons, the defocus profiles are presented in millimeters, with 1 mm being approximately 4 D in the IOL plane. As can be seen from the simulations presented in FIGS. 4A-4C, the depth of focus for each of the lens profiles incorporating a cubic phase profile is extended as compared to the monofocal lens.

Figure 5A:
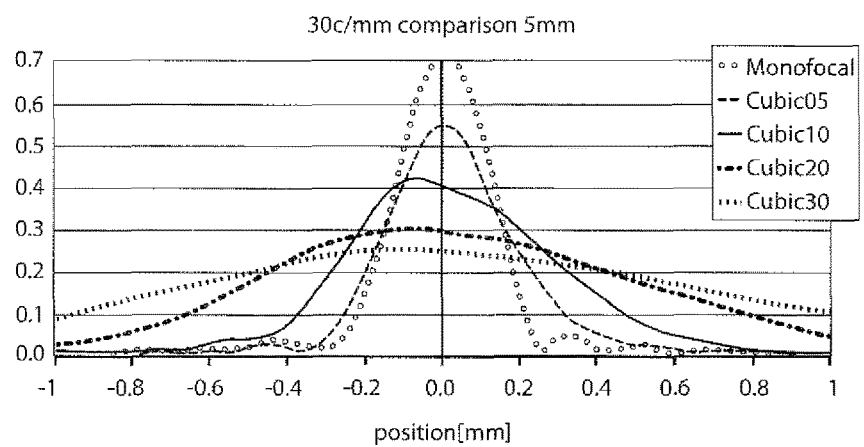
FIGS. 5A-5C illustrate modeled MTF-defocus curve comparisons for white light and a 5 mm pupil between lenses according to embodiments of the invention.
Figure 5B:
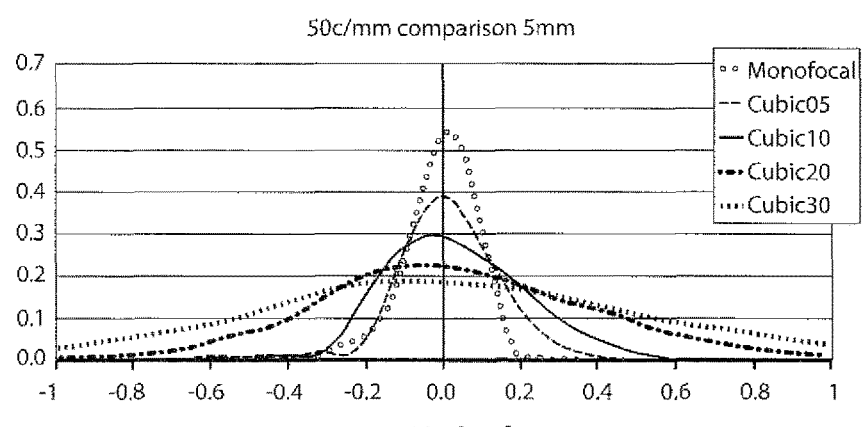
Figure 5C:
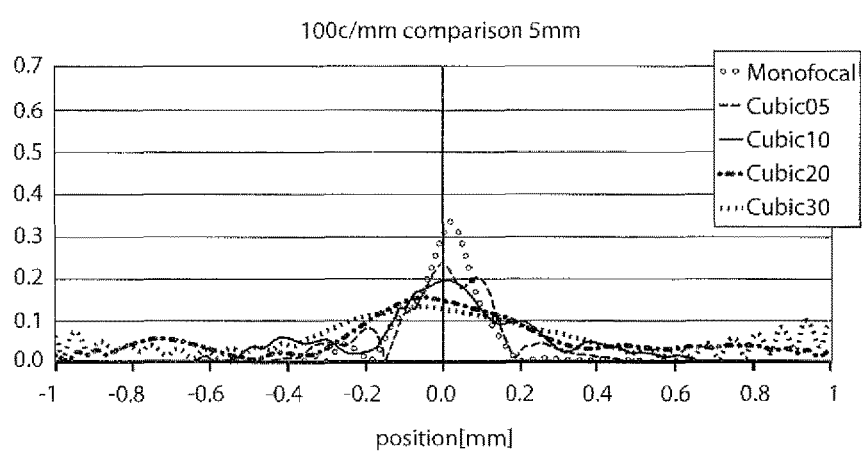

FIGS. 5A-5C show simulated white light MTF results at three different spatial frequencies for simulated IOLs incorporating a cubic phase profile using a 5 mm pupil and the same rotationally symmetric theoretical eye model, and comparing those profiles to a monofocal IOL. In each of these comparisons, the defocus profiles are presented in millimeters, with 1 mm being approximately 4 D in the IOL plane. As can be seen from the simulations presented in FIGS. 5A-5C, the depth of focus for each of the lens profiles incorporating a cubic phase profile is extended as compared to the monofocal lens.

Other higher order phase profiles may also be incorporated into a lens to further improve the depth of field. As a preferred example, a pentic phase profile may be incorporated into the base profile. In another preferred example, the cubic phase profile may also be incorporated, to improve the depth of field resulting in an overall profile given by the equation:

Profile=Base Profile+Cubic Phase Profile+Pentic Phase Profile,

As with the cubic phase profile alone, the base profile in the calculation above is preferably optimized for desired focal properties prior to incorporation of the cubic and pentic phase profiles. Yet more preferably, the base profile has an aspheric component, with at least the aspheric component being optimized prior to incorporation of the cubic and/or pentic phase profile. Optimization is preferably performed to make the tail of the depth of focus curve hyperopic.

Figure 6:
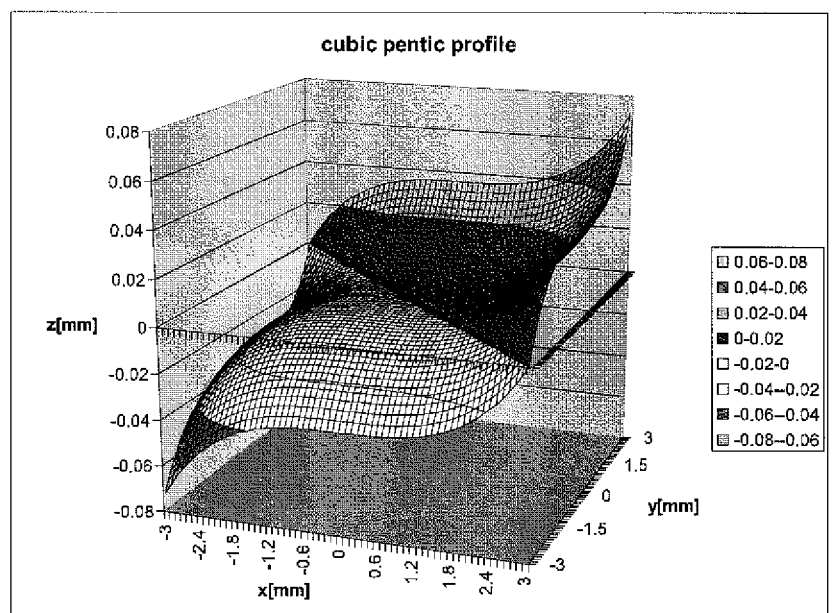
FIG. 6 illustrates a cubic pentic profile.

The pentic phase profile has a curvature that is defined by the following function:

$$f(x,y)=C(x^5+y^5),$$

wherein C is a scalar value that may be optimized to help achieve the desired depth of field (along with optimization of the scalar A from the cubic phase profile). FIG. 6 illustrates the combination of cubic and pentic phase profiles as a surface profile. As illustrated, this cubic pentic phase profile is not rotationally symmetric, but rather it is point symmetric. As is the case with a cubic phase profile, the average phase contribution from the cubic pentic phase profile, over the pupil, will be zero, so that there will be no phase shift added to the lens regardless of the pupil size. Also, because of the extended depth of focus, a lens incorporating a cubic pentic phase profile is anticipated to improve halo and glare performance with respect to a multifocal lens.

Figure 7A:
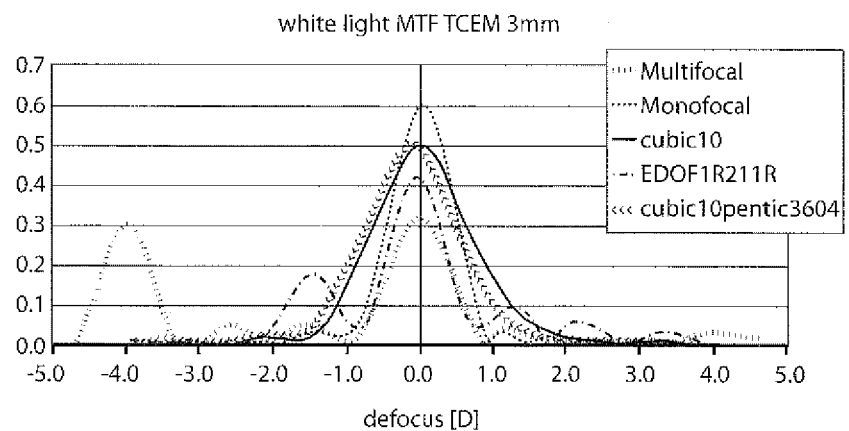
FIGS. 7A and 7B illustrate modeled MTF-defocus curve comparisons for white light between lenses according to embodiments of the invention.

FIG. 7A illustrates simulated white light MTF results at a spatial frequency of 50 c/mm for simulated 20 D IOLs, one incorporating a cubic phase profile, and another incorporating a cubic pentic profile, using a 3 mm pupil and the same rotationally symmetric theoretical eye model, and comparing those profiles to monofocal and multifocal IOLs. For the cubic pentic profile, A=−0.0010 and C=0.000360456181. In each of these comparisons, the defocus profiles are presented over 5 D in the IOL plane. As can be seen from the simulations illustrated in FIG. 7A, the depth of focus for each of the lens profiles incorporating either a cubic phase profile or a cubic pentic profile is extended as compared to the monofocal and multifocal lenses.

Figure 7B:
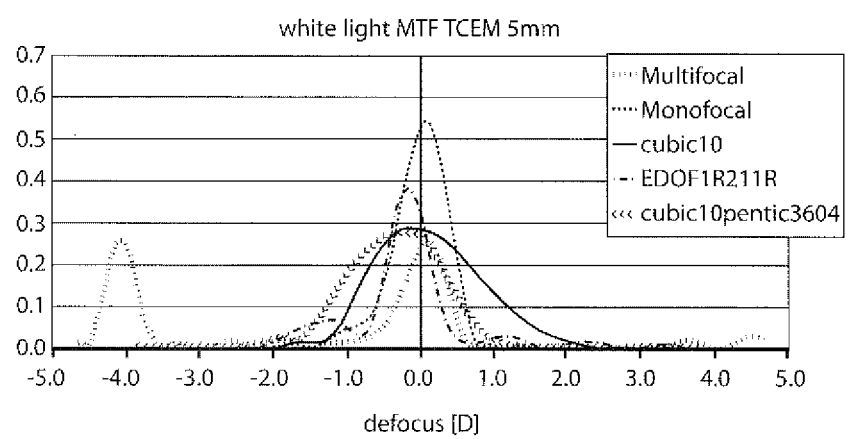
Figure 8A:
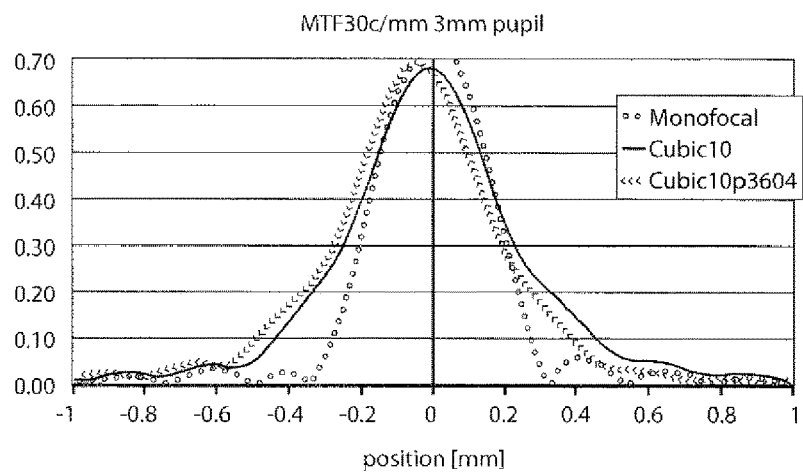
FIGS. 8A-8C illustrate modeled MTF-defocus curve comparisons for white light and a 3 mm pupil between lenses according to embodiments of the invention.
Figure 8B:
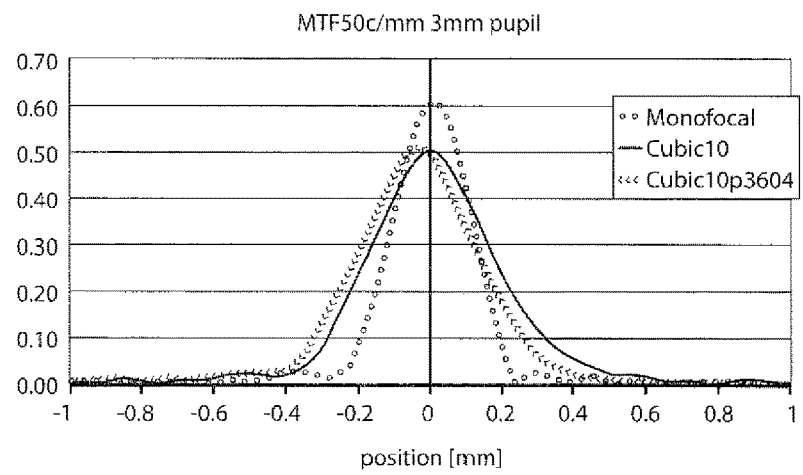
Figure 8C:
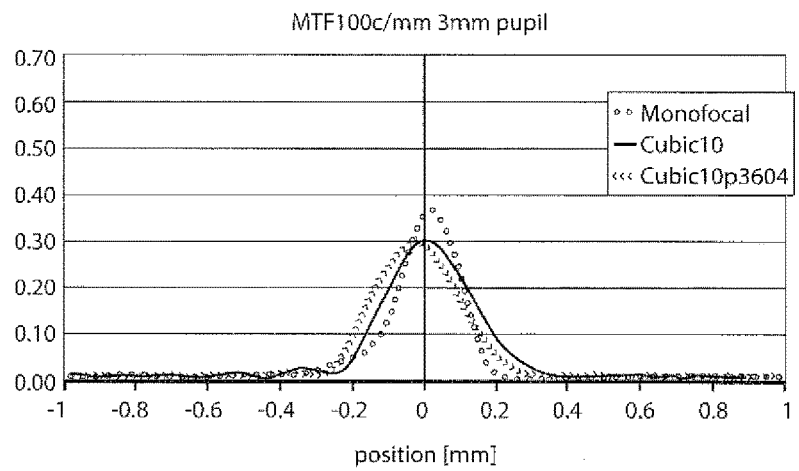

FIG. 7B illustrates simulated white light MTF results at a spatial frequency of about 50 c/mm for simulated 20 D IOLs, one incorporating a cubic phase profile, and another incorporating a cubic pentic profile, using a 5 mm pupil and the rotationally symmetric theoretical eye model, and comparing those profiles to monofocal and multifocal IOLs. For the cubic pentic profile, A=−0.0010 and C=0.000360456181. In each of these comparisons, the defocus profiles are presented over 5 D in the IOL plane. As can be seen from the simulations presented in FIG. 7B, the depth of focus for each of the lens profiles incorporating either a cubic phase profile or a cubic pentic profile is extended as compared to the monofocal and multifocal lenses.

Figure 9A:
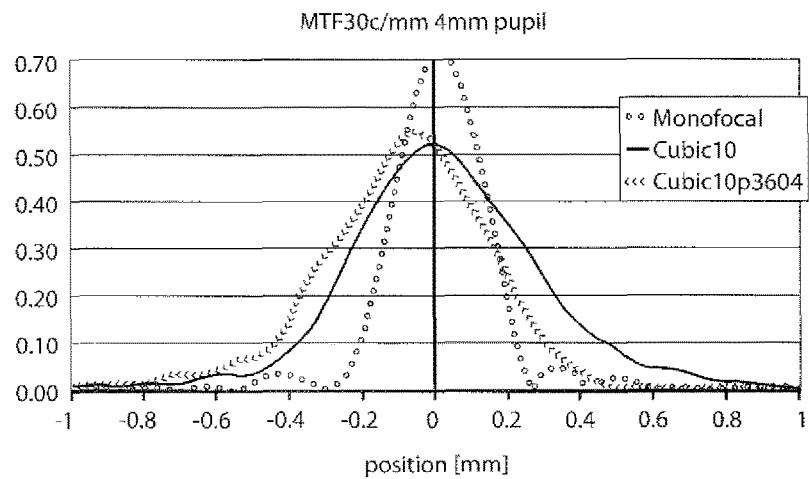
FIGS. 9A-9C illustrate modeled MTF-defocus curve comparisons for white light and a 4 mm pupil between lenses according to embodiments of the invention.
Figure 9B:
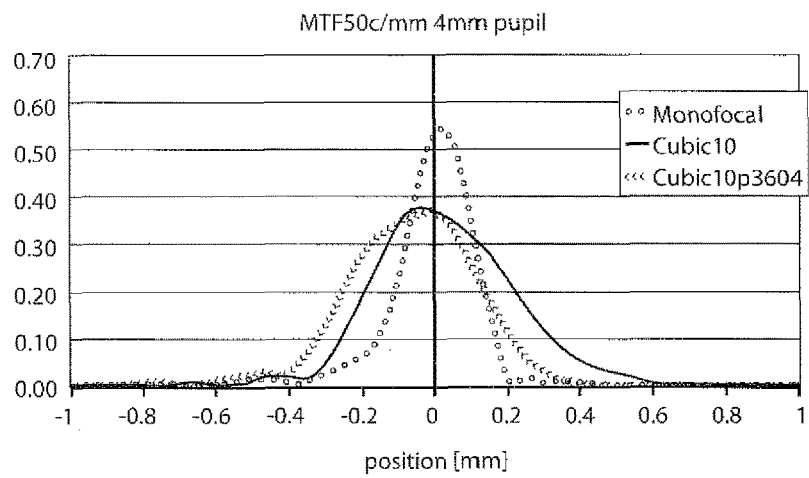
Figure 9C:
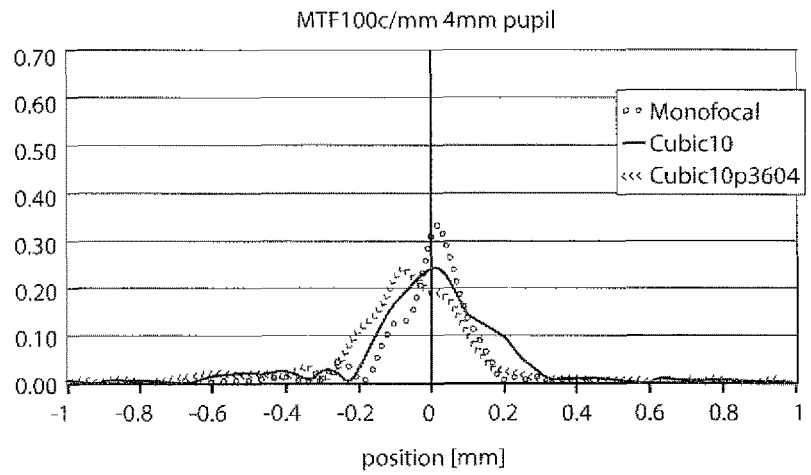

FIGS. 9A-9C illustrate simulated white light MTF results at three different spatial frequencies for simulated IOLs incorporating either a cubic phase profile or a cubic pentic profile, using a 4 mm pupil and the rotationally symmetric theoretical eye model, and comparing those profiles to a monofocal IOL. In each of these comparisons, the defocus profiles are presented in millimeters, with 1 mm being approximately 4 D in the IOL plane. As can be seen from the simulations presented in FIGS. 9A-9C, the depth of focus for each of the lens profiles incorporating either a cubic phase profile or a cubic pentic phase profile is extended as compared to the monofocal lens.

Figure 10A:
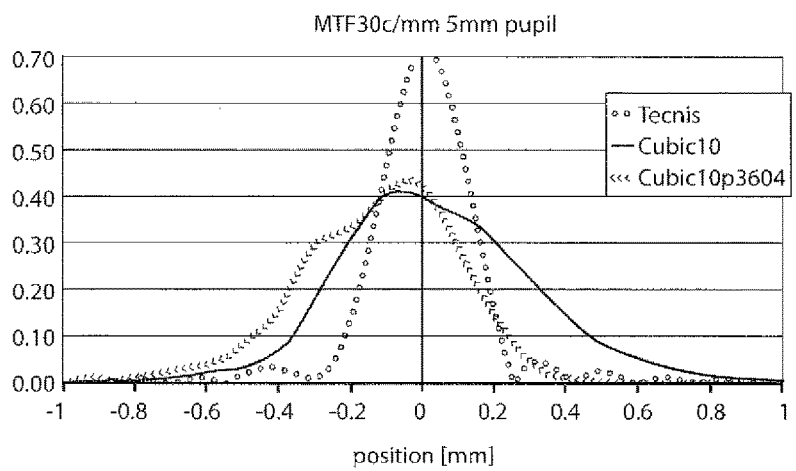
FIGS. 10A-10C illustrate modeled MTF-defocus curve comparisons for white light and a 5 mm pupil between lenses according to embodiments of the invention.
Figure 10B:
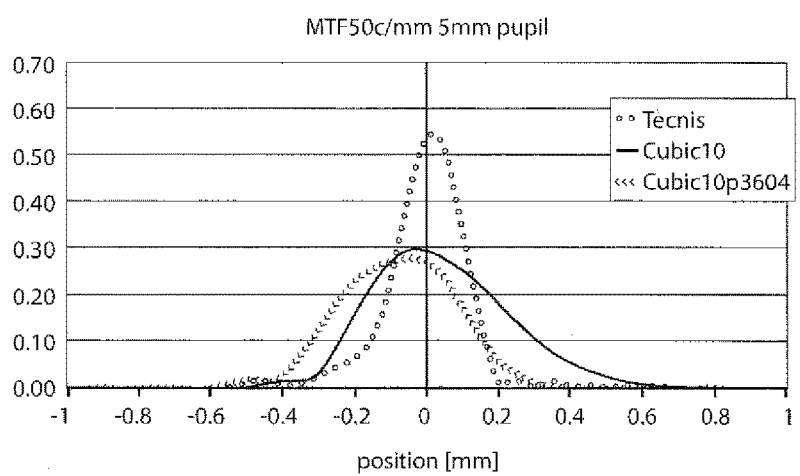
Figure 10C:
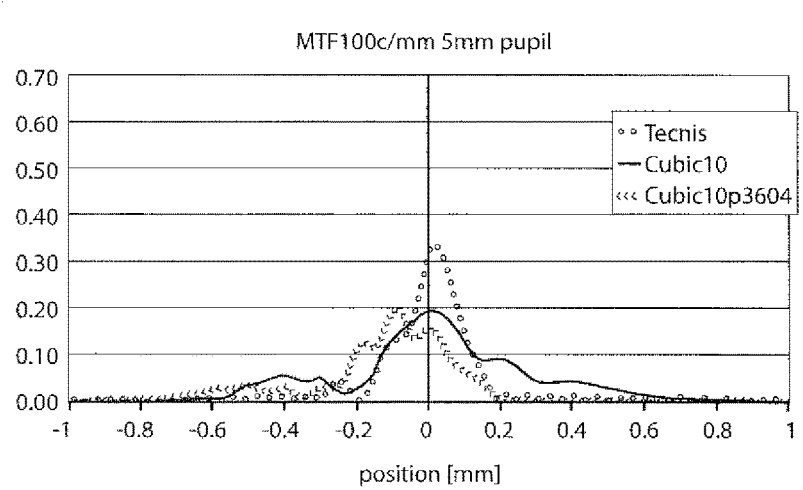

FIGS. 10A-10C illustrate simulated white light MTF results at three different spatial frequencies for simulated IOLs incorporating either a cubic phase profile or a cubic pentic profile, using a 5 mm pupil and the rotationally symmetric theoretical eye model, and comparing those profiles to a monofocal IOL. In each of these comparisons, the defocus profiles are presented in millimeters, with 1 mm being approximately 4 D in the IOL plane. As can be seen from the simulations presented in FIGS. 10A-10C, the depth of focus for each of the lens profiles incorporating either a cubic phase profile or a cubic pentic phase profile is extended as compared to the monofocal lens.

Figure 11A:
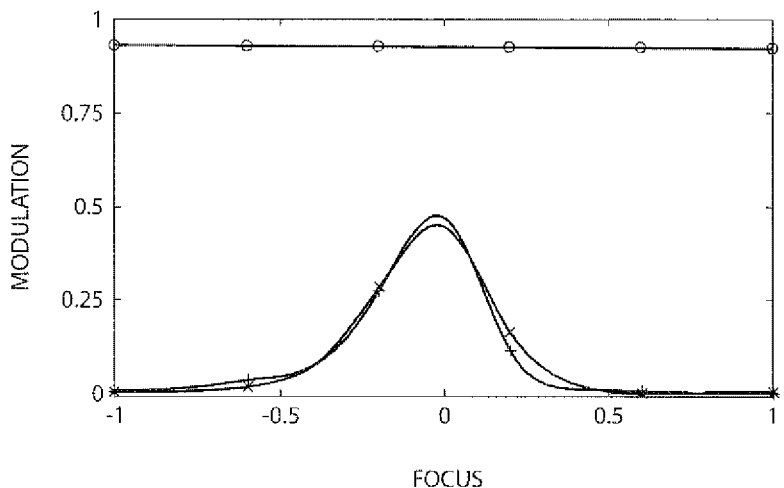
FIGS. 11A-11B illustrate modeled MTF-defocus curve comparisons for non-rotationally symmetric lenses according to embodiments of the invention.
Figure 11B:
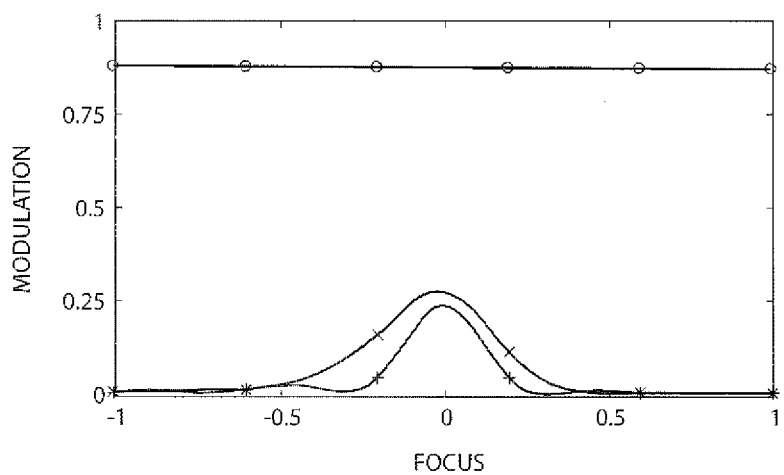

FIG. 11A illustrates a comparison between simulated white light MTF results at a spatial frequency of 30 dim for a cubic pentic design in the sagital direction and in the meridional direction of an IOL. FIG. 11B shows a comparison between simulated white light MTF results at a spatial frequency of 50 c/mm for a cubic pentic design in the sagital direction and in the meridional direction of an IOL. Both simulations use the rotationally symmetric theoretical eye model. As can be seen by comparison of FIGS. 11A and 11B, the difference in the results at a spatial frequency of 30 c/mm is negligible, while there is a more pronounced difference in the results at a spatial frequency of 50 c/mm is more pronounced.

Figure 12A:
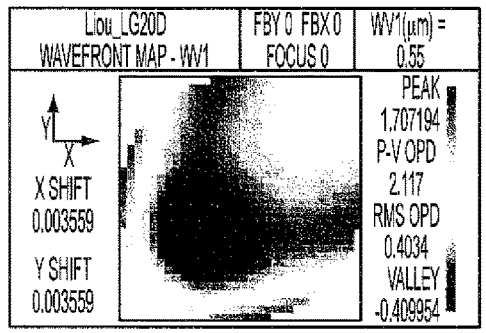
FIGS. 12A-12H illustrate modeled wavefront profiles for non-rotationally symmetric lenses according to embodiments of the invention.
Figure 12B:
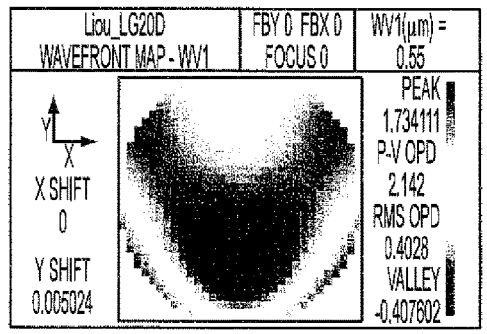
Figure 12C:
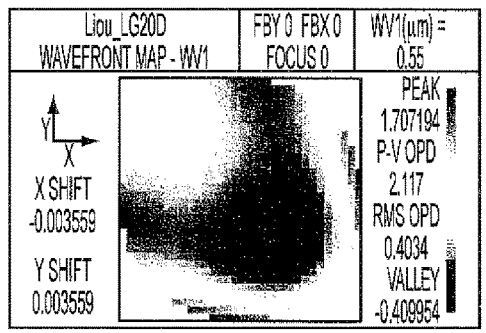
Figure 12D:
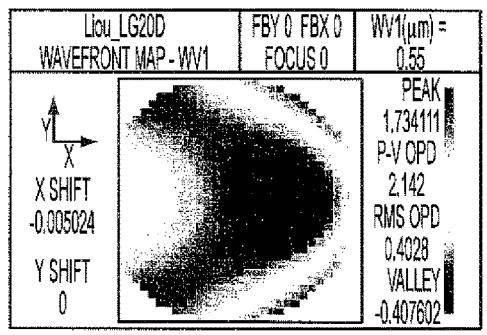
Figure 12E:
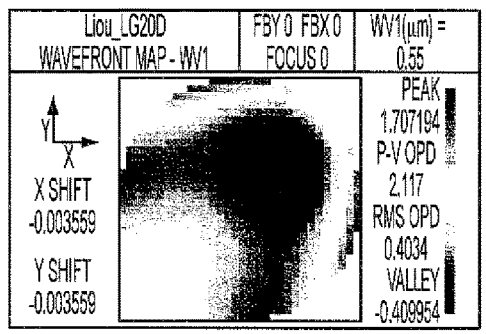
Figure 12F:
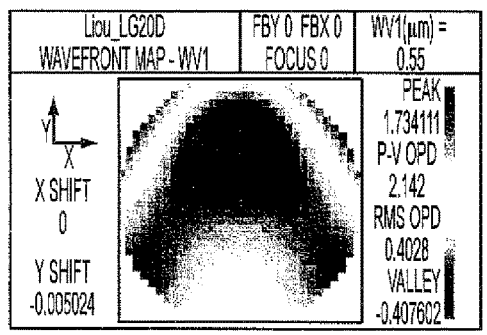
Figure 12G:
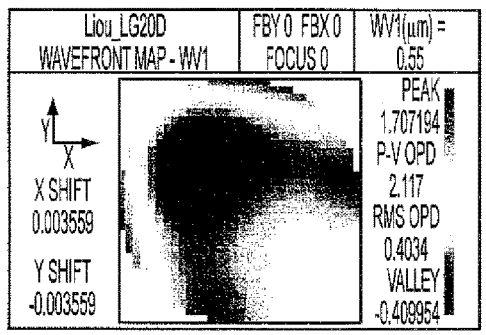
Figure 12H:
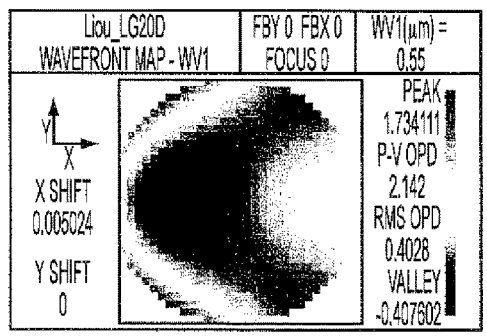

FIGS. 12A-12H illustrate simulated wavefronts that result from incorporation of a cubic pentic phase profile into a base profile of an IOL using a 4 mm pupil and the rotationally symmetric theoretical eye model. The wavefront of FIG. 12A is defined as a rotation of zero degrees for the IOL, and each subsequent figure in the sequence shows the resulting wavefront from a rotation of the IOL by an additional 45 degrees. As can be seen, the wavefront profiles have coma-like features, and these features have an orientation that corresponds to the orientation of the IOL.

Figure 13A:
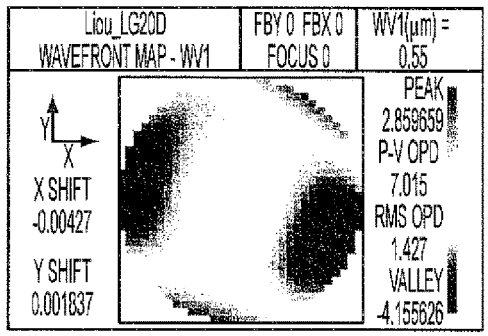
FIGS. 13A-13P illustrate modeled wavefront profiles for non-rotationally symmetric lenses according to embodiments of the invention.
Figure 13B:
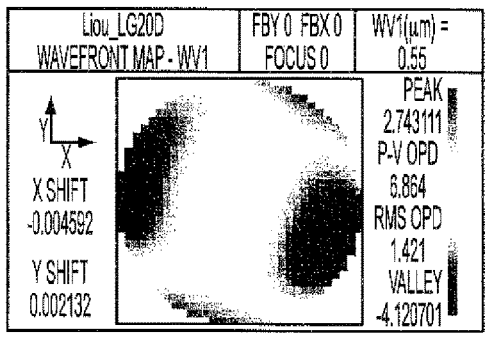
Figure 13C:
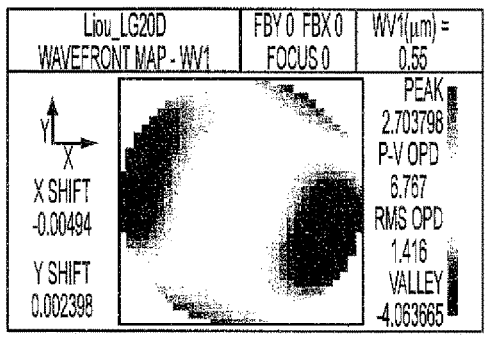
Figure 13D:
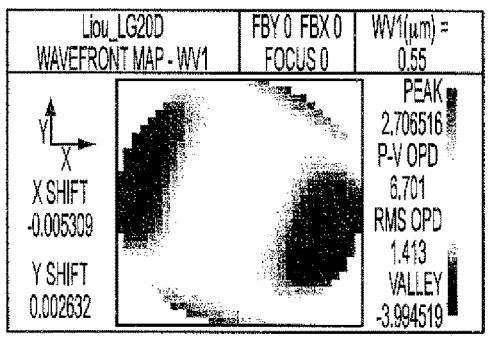
Figure 13E:
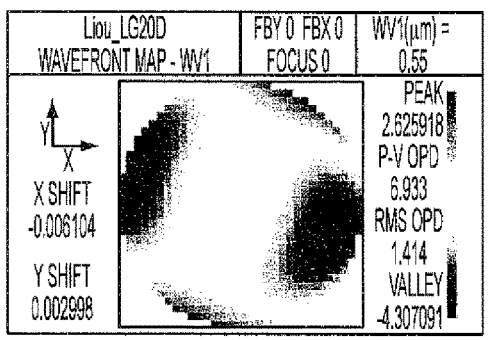
Figure 13F:
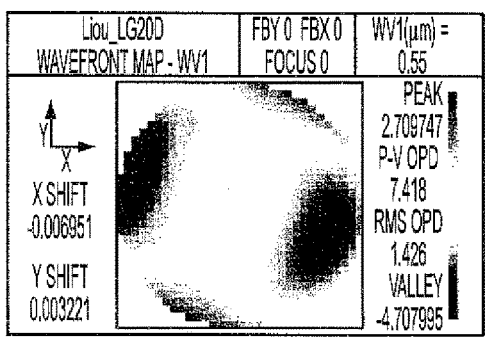
Figure 13G:
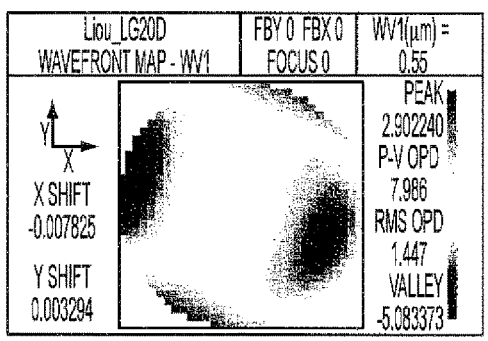
Figure 13H:
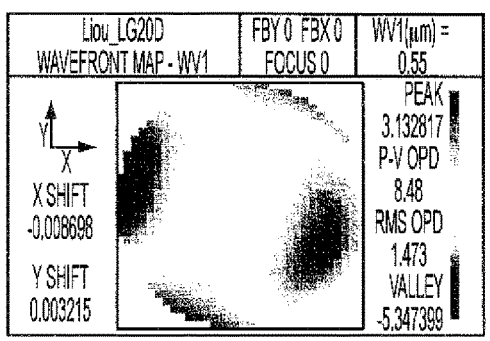
Figure 13I:
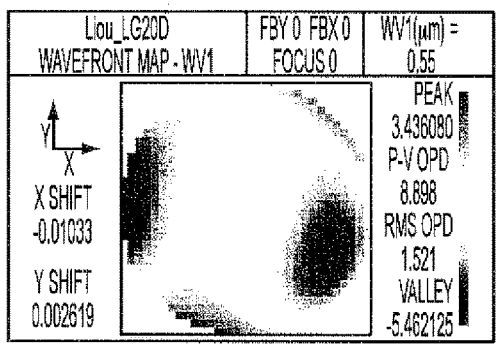
Figure 13J:
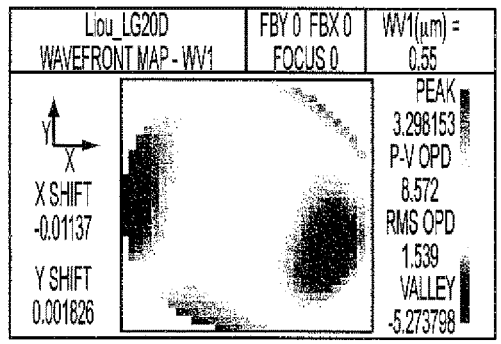
Figure 13K:
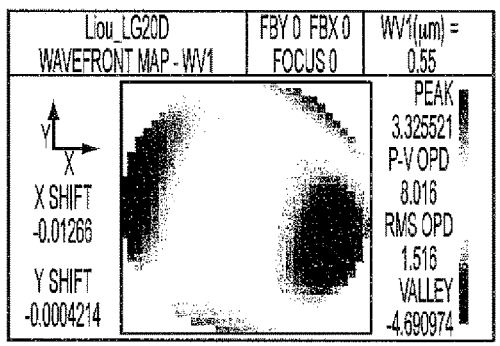
Figure 13L:
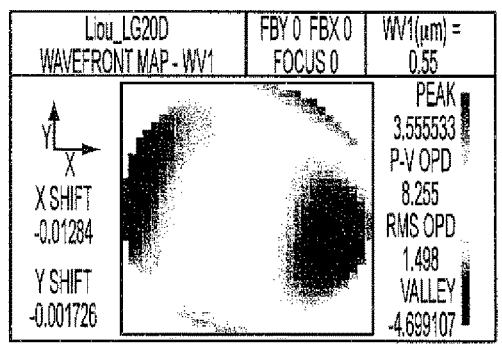
Figure 13M:
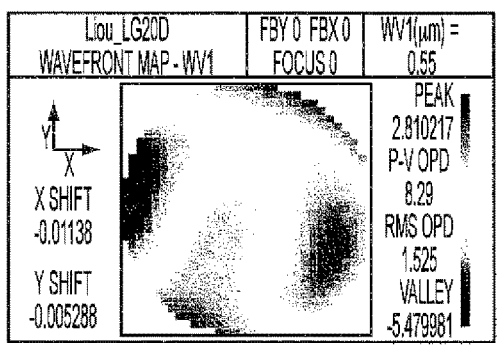
Figure 13N:
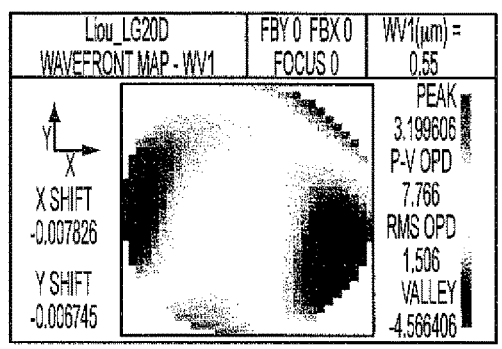
Figure 13O:
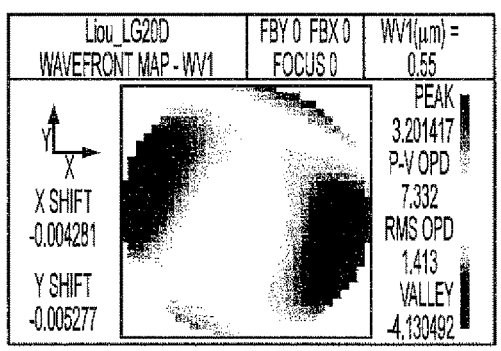
Figure 13P:
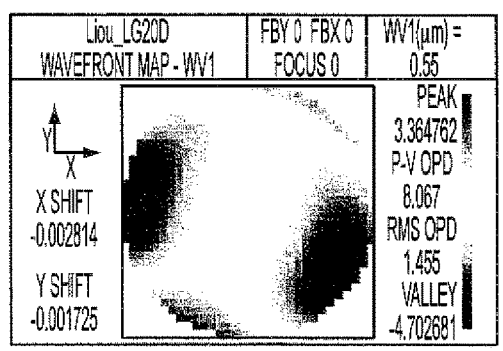

FIGS. 13A-13P illustrate simulated wavefronts that result from incorporation of a cubic pentic phase profile into a base profile of an IOL using a 4 mm pupil and an optical model of an eye (the model includes aberrations that may be found in an individual's eye). The wavefront of FIG. 13A is defined as a rotation of zero degrees for the IOL, and each subsequent figure in the sequence shows the resulting wavefront from a rotation of the IOL by an additional 15 degrees. As can be seen, the wavefront profiles may have coma-like features, but for this more realistic model, the orientation of the wavefront does not rotate along with rotation of the IOL. Instead, the orientation of the wavefront remains constant, with changes resulting in the quality of the focus of the wavefront. Within FIGS. 13A-13P, FIG. 13B, at an IOL rotation of 15 degrees, appears to present the optimal orientation. Depending upon the IOL, the scalar values used for the cubic and pentic profiles, and the eye to which the IOL is fitted and optimized for, the optimal orientation of the IOL may change.

Further balancing and optimization may be achieved by optimizing asphericity. For example, when C=0, the peak optical performance may be in the middle of the focus profile. Ideally, good far image quality is desired for every patient irrespective of conditions, such that a value for C other than zero may emphasis the optimized location on a profile for far focus.

A cubic and/or pentic phase profile may also be used for wavefront coding and digital imaging processing in applications in need of an extended depth of field, such as in combination with retinal implants or iris recognition programs, for example. Further, outside use with retinal implants, when decoding by the retinal is not possible the cubic and/or pentic phase profile addition should leave enough image quality such that the cubic and/or pentic phase profile may, on average, have a zero addition of phase irrespective of pupil size and MTF performance and independent of orientation.

Figure 14:
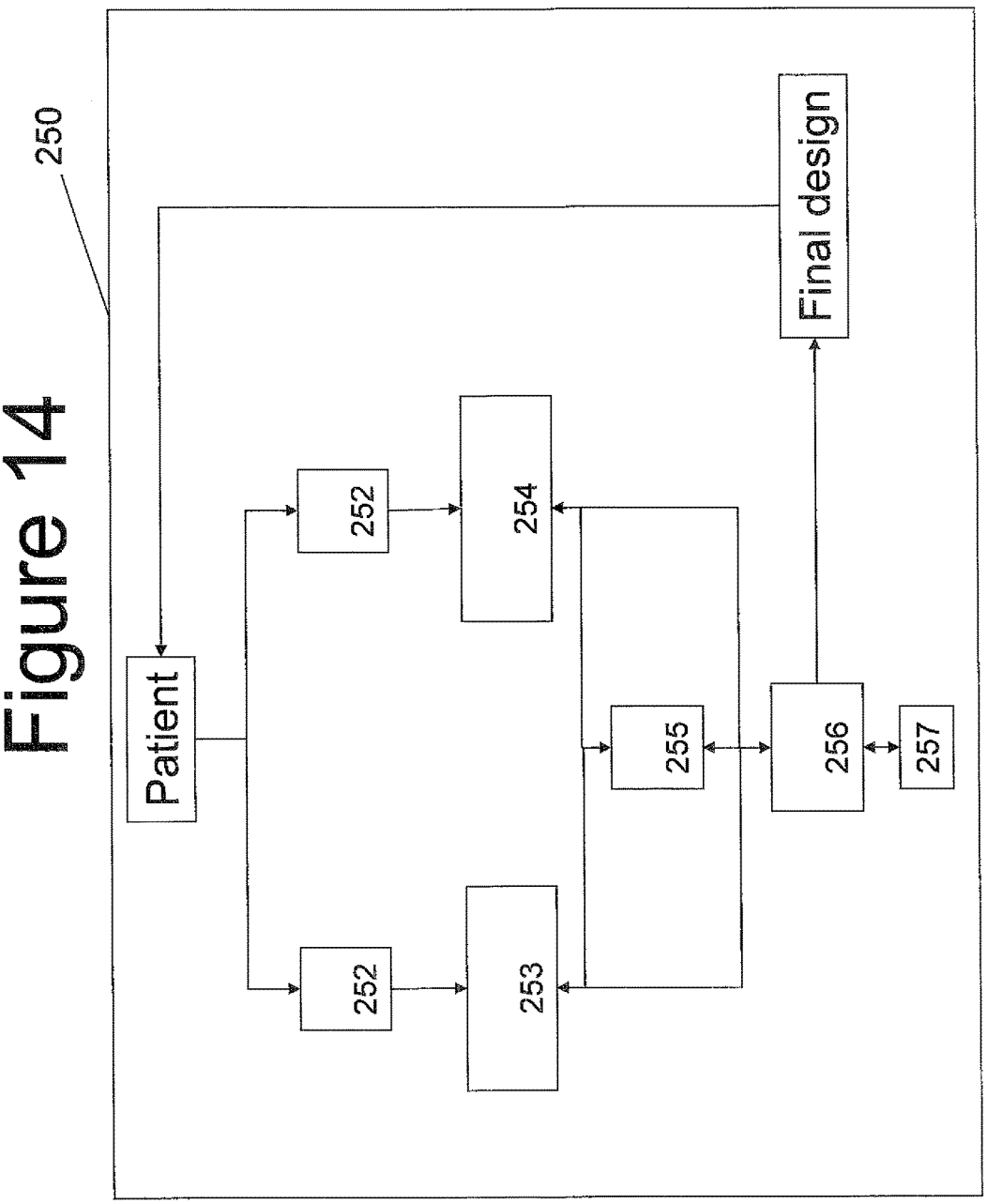
FIG. 14 is a flow diagram illustrating a method in accordance with the invention.

FIG. 14 illustrates a method 250 of providing a lens according the invention discussed hereinthroughout. The method 250 may include the steps of assessing the biometrics of the eye at step 252. For example, step 252 may further include questions related to the patient's life style (common habits, work, etc.) at step 253, such as to define an optimal lens performance at step 254. The output of steps 252, 253 and 254 may, in combination, allow for a determination of a preferred lens profile(s) at step 255. Step 256 may additionally include further customizations design, such as for particular enhancements of far, near and/or intermediate vision. At step 257, simulations may be used to indicate any aberrations resultant from the profile(s) developed at steps 255 and/or 256, and at step 257 any required remedial measures to treat such aberrations may be fed back to the design of steps 253, 254 and 255, for the final lens design. Those skilled in the art will appreciate that certain of the steps of method 250 may be performed using computing and/or simulations, and that some or all steps may or may not be carried out by certain actors, such as, but not including, a lens designer, a lens manufacturer, or a surgeon, by way of example.

Figure 15:
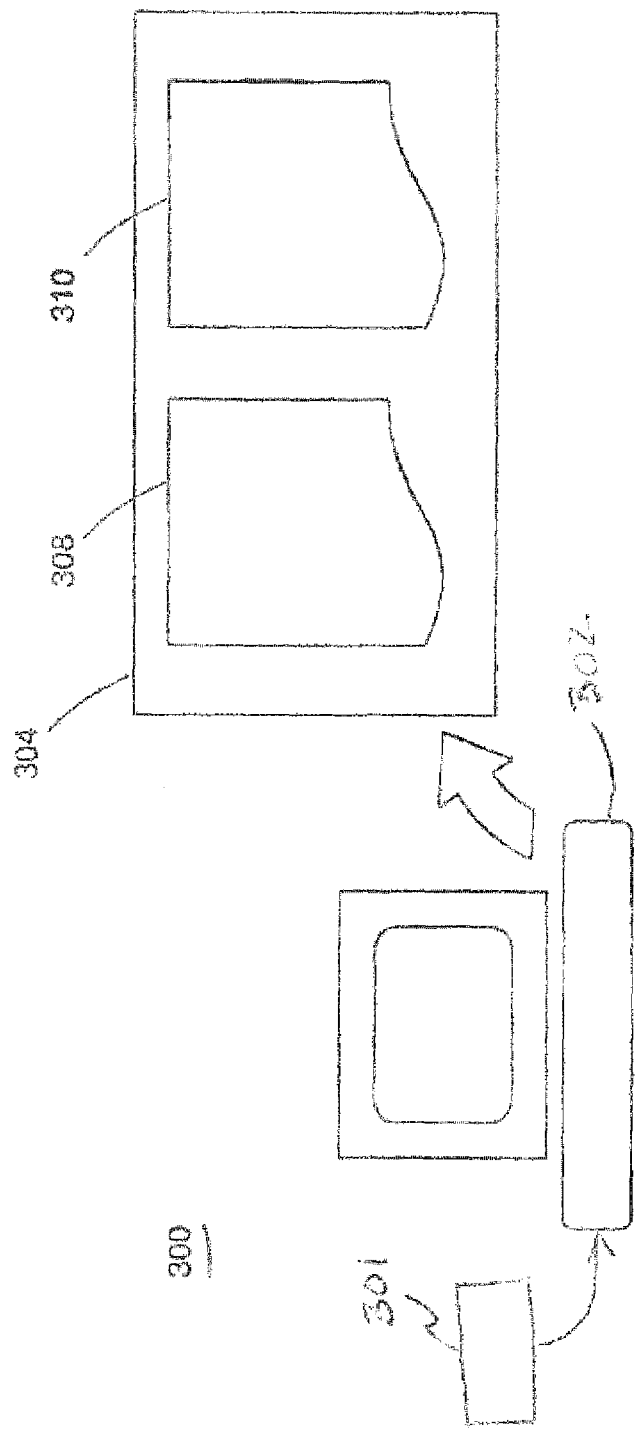
FIG. 15 is a schematic block diagram illustrating a computing system for use with the embodiments of the present invention

As illustrated in FIG. 15, the present invention may be implemented in a clinical system 300 that is capable of assessing the eye's biometric measurements and of performing the calculations set forth in method 250. The system 300 may include a biometric reader 301 that may take or formulate measurements needed for at least a base power calculation 301, a processor 302, and a computer readable memory 304 coupled to the processor 302. The computer readable memory 304 includes therein an array of ordered values 308 and sequences of instructions 310 which, when executed by the processor 302, cause the processor 302 to design an IOL configured for implantation into the eye. The array of ordered values 308 may comprise data used or obtained from method 250 or other methods consistent with embodiments of the invention. The sequence of instructions 310 may include one or more steps of method 250 or other methods consistent with embodiments of the invention.

The processor 302 may be embodied in a general purpose desktop or laptop computer, and/or may comprise hardware associated with biometric reader 301 specifically for selecting an IOL consistent with the embodiments of the invention. In certain embodiments, the system 300 may be configured to be electronically coupled to another device, such as one or more instruments for obtaining measurements of an eye or a plurality of eyes. Alternatively, the system 300 may be embodied in a handheld device that may be adapted to be electronically and/or wirelessly coupled to one or more other devices.

Thus, a lens having an extended depth of focus, and a method relating to same, is disclosed. While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. An ophthalmic lens having an extended depth of focus, comprising:
    an anterior face; and
    a posterior face,
    wherein at least a portion of one of the anterior face and the posterior face comprises a curvature defined by a summation of a cubic phase profile defined by $f(x,y)=A(x^3+y^3)$ and a pentic phase profile defined by $f(x,y)=C(x^5+y^5)$, wherein C is a scalar value, wherein the ophthalmic lens is configured to provide a white light MTF of at least 0.2 over a range of at least 2.0 D, wherein the ophthalmic lens is configured for placement adjacent a pupil such that an average phase contribution from the curvature over the pupil is zero, wherein the ophthalmic lens is configured to produce wavefront profiles having coma features in a rotationally symmetric theoretical eye model having a 4 mm pupil, and wherein an orientation of the wavefront profiles having the coma features remains constant with rotation of the ophthalmic lens.

2. The ophthalmic lens of claim 1, wherein all of one of the anterior face and the posterior face comprises the curvature.

3. The ophthalmic lens of claim 1, wherein C is 0.000360456181.

4. The ophthalmic lens of claim 1, wherein A is selected from the group consisting of −0.0005, −0.0010, −0.0020, and −0.0030.

* * * * *